(12) United States Patent
Lee et al.

(10) Patent No.: US 11,237,114 B2
(45) Date of Patent: Feb. 1, 2022

(54) HYDROGEL BEAD, CHEMICAL SENSOR INCLUDING THE SAME, CONTAINER AND ELECTRONIC ARTICLE INCLUDING THE CHEMICAL SENSOR

(71) Applicant: KOOKMIN UNIVERSITY INDUSTRY ACADEMY COOPERATION FOUNDATION, Seoul (KR)

(72) Inventors: Hyun Jung Lee, Seoul (KR); Soo Hyun Kim, Cheonan-si (KR); Mi Rim Ham, Wonju-si (KR)

(73) Assignee: KOOKMIN UNIVERSITY INDUSTRY ACADEMY COOPERATION FOUNDATION, Seoul (KR)

( * ) Notice: Subject to any disclaimer, the term of this patent is extended or adjusted under 35 U.S.C. 154(b) by 0 days.

(21) Appl. No.: 16/838,837

(22) Filed: Apr. 2, 2020

(65) Prior Publication Data
US 2020/0319114 A1    Oct. 8, 2020

(30) Foreign Application Priority Data
Apr. 3, 2019 (KR) .................. 10-2019-0039268

(51) Int. Cl.
*G01N 21/80* (2006.01)
*G01N 21/78* (2006.01)
(Continued)

(52) U.S. Cl.
CPC ............ *G01N 21/80* (2013.01); *G01N 21/78* (2013.01); *G01N 21/783* (2013.01);
(Continued)

(58) Field of Classification Search
CPC .......... G01N 2021/7723; G01N 21/77; G01N 21/78; G01N 21/783; G01N 21/80; G01N 31/22; G01N 31/221; G01N 31/223; G01N 33/02; Y10T 436/143333; Y10T 436/15; Y10T 436/16; Y10T 436/175383; Y10T 436/204998
USPC ...... 422/400, 401, 402, 83, 86, 547; 436/20, 436/79, 94, 103, 113, 133, 100, 163, 164, 436/165
See application file for complete search history.

(56) References Cited

U.S. PATENT DOCUMENTS 9,983,141 B2    5/2018  Jung et al.
2006/0057022 A1*  3/2006  Williams ............... G01N 31/22
                                                   422/400
(Continued)

FOREIGN PATENT DOCUMENTS

KR    1020160001509 A    1/2016

OTHER PUBLICATIONS

Zhang et al. Food Hydrocolloids, vol. 65, Nov. 18, 2016, pp. 198-205.*
(Continued)

*Primary Examiner* — Maureen Wallenhorst
(74) *Attorney, Agent, or Firm* — Sughrue Mion, PLLC

(57) ABSTRACT

Disclosed herein are a hydrogel bead, a chemical sensor including the same, and an electronic product including the chemical sensor. The hydrogel bead includes at least one type of polysaccharide physically crosslinked with a cation or an anion, and a pH indicator dye.

14 Claims, 12 Drawing Sheets

(51) Int. Cl.
*G01N 31/22* (2006.01)
*G01N 33/02* (2006.01)

(52) U.S. Cl.
CPC ......... *G01N 31/221* (2013.01); *G01N 31/223* (2013.01); *G01N 33/02* (2013.01); *Y10T 436/175383* (2015.01); *Y10T 436/204998* (2015.01)

(56) References Cited

U.S. PATENT DOCUMENTS

| | | | | |
|---|---|---|---|---|
| 2015/0377791 | A1* | 12/2015 | Jung | G01N 31/221 436/55 |
| 2016/0146739 | A1* | 5/2016 | Lee | G01N 31/22 422/430 |
| 2017/0326275 | A1* | 11/2017 | Lecler | A61K 9/08 |
| 2018/0055777 | A1* | 3/2018 | McClements | A23P 10/30 |

OTHER PUBLICATIONS

Spiess et al. Chemical Engineering Science, vol. 63, Apr. 6, 2008, pp. 3457-3465.*
Pauly et al. Journal of Biotechnology, vol. 280, Jun. 5, 2018, pp. 42-48.*
K.L. Deng et al., "Drug release behavior of a pH/temperature sensitive calcium alginate/poly(N-acryloylglycine) bead with core-shelled structure", Express Polymer Letters, vol. 4, No. 12, 2010, pp. 773-780 ( 8 pages total).
Piyasi Mukhopadhyay et al., "Formulation of pH-Responsive Carboxymethyl Chitosan and Alginate Beads for the Oral Delivery of Insulin", Journal of Applied Polymer Science, 2013, pp. 835-845 (11 pages total).

* cited by examiner

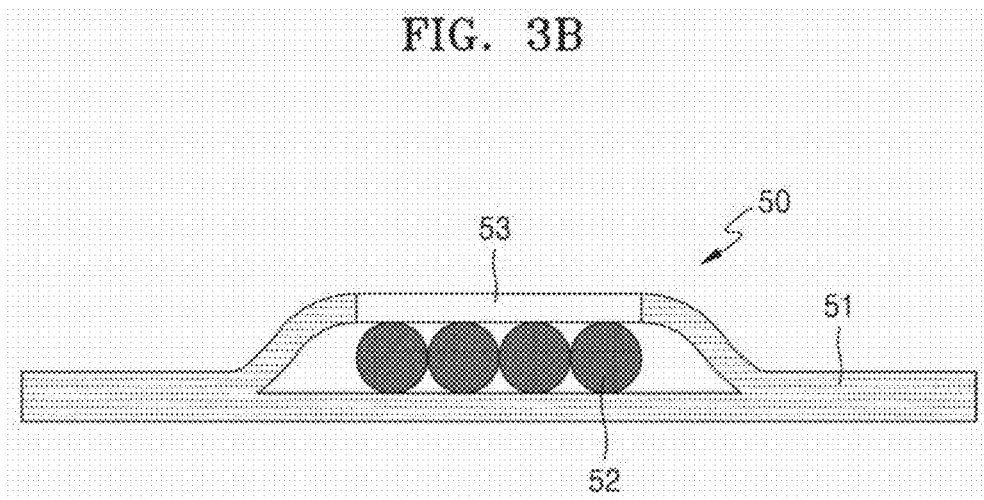

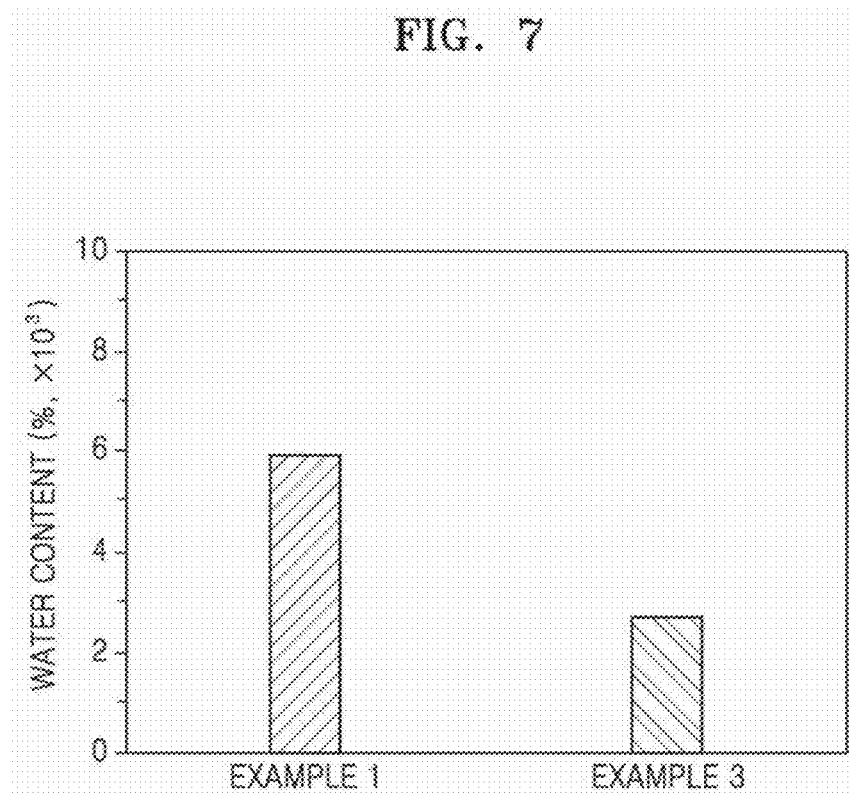

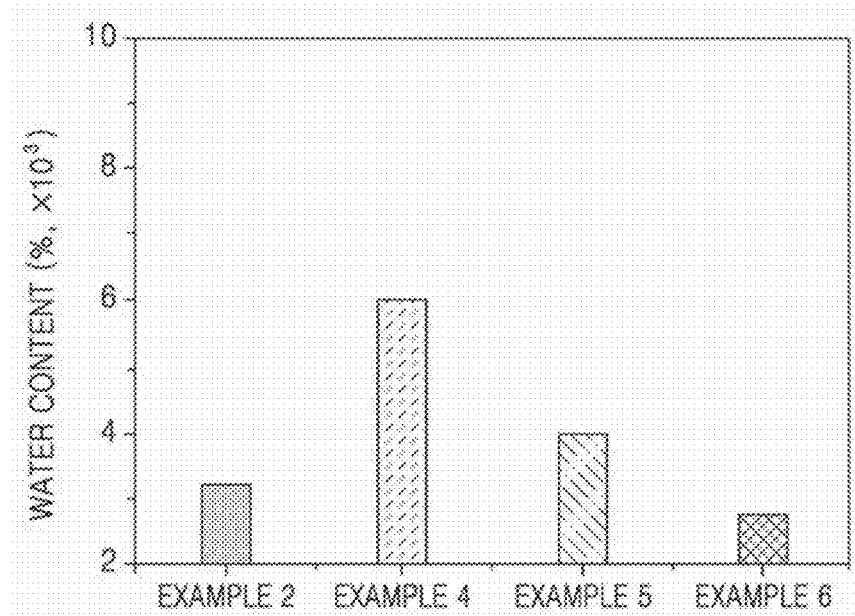

HYDROGEL BEAD, CHEMICAL SENSOR INCLUDING THE SAME, CONTAINER AND ELECTRONIC ARTICLE INCLUDING THE CHEMICAL SENSOR

CROSS-REFERENCE TO RELATED APPLICATION

This application claims the benefit of Korean Patent Application No. 10-2019-0039268, filed on Apr. 3, 2019, in the Korean Intellectual Property Office, the disclosure of which is incorporated herein in its entirety by reference.

BACKGROUND

1. Field

One or more embodiments relate to a hydrogel bead, a chemical sensor including the same, and a container and electronic product including the chemical sensor.

2. Description of Related Art

As a food sensor that checks the stability of food, a biosensor and/or a gas sensor are mainly used depending on an object of a substance to be detected and a receptor thereof. Furthermore, a sensor may also be used when checking the fermentation and spoilage states of food by detecting harmful substances such as ammonia, hydrogen sulfide, acetic acid, and carbon dioxide, which are generated during food fermentation.

A kimchi refrigerator, which is currently widely used, includes only a cooling function capable of controlling the fermentation degree by adjusting the temperature. However, there are many cases in which users cannot be satisfied with this temperature control function, and when using a kimchi refrigerator only for storage, a user frequently opens a storage container to check the condition of kimchi, leading to bringing kimchi into contact with air, and thus changes in taste and freshness of kimchi may frequently occur.

Therefore, there is still a need for a novel sensor material that detects, in addition to the stability of food, the fermentation degree, putrefaction of food, or spoilage degree, a sensor including the same, and the like.

SUMMARY

One or more embodiments include a hydrogel bead which is portable and facilitates the detection of harmful substances present in food within a wide range of pH.

One or more embodiments include a chemical sensor including the hydrogel bead.

One or more embodiments include a container including the chemical sensor.

One or more embodiments include an electronic product including the container.

Additional aspects will be set forth in part in the description which follows and, in part, will be apparent from the description, or may be learned by practice of the presented embodiments of the disclosure.

According to one or more embodiments, a hydrogel bead includes:
at least one type of polysaccharide physically crosslinked with a cation or an anion; and a pH indicator dye.

The hydrogel bead may include a single-bead type, a core-shell bead type, or a combination thereof.

The hydrogel bead may be a single-bead type in which the pH indicator dye is distributed in the at least one type of polysaccharide physically crosslinked with a cation or an anion.

The hydrogel bead may be a core-shell bead type consisting of: a core including a first polysaccharide physically crosslinked with the cation and a pH indicator dye; and a shell including, on the core, a second polysaccharide, the second polysaccharide being non-crosslinked.

The hydrogel bead may be a core-shell bead type consisting of: a core including a second polysaccharide physically crosslinked with the anion and a pH indicator dye; and a shell including, on the core, a first polysaccharide, the first polysaccharide being non-crosslinked.

The cation may include $Ca^{2+}$.

The anion may include $P_3P_{10}^{5-}$.

The polysaccharide may include alginate, chitosan, or a combination thereof.

The pH indicator dye may be a dye that causes color conversion when a target material is diffused in an aqueous solution inside the hydrogel bead.

The target material may include carbon dioxide, acetic acid, ammonia, or a combination thereof.

The pH indicator dye may be a dye that causes color conversion within a pH ranging from about 3.5 to about 6.0.

The pH indicator dye may be selected from bromophenol blue (BPB), bromothymol blue (BTB), bromocresol purple (BCP), bromocresol green (BCG), metacresol purple (mCP), and a mixture thereof.

According to one or more embodiments,
a chemical sensor includes the above-described hydrogel bead.

The chemical sensor may include a patch-type chemical sensor, a pouch-type chemical sensor, a pocket-type chemical sensor, or a combination thereof.

The hydrogel bead may be arranged, without a support, on an inner surface of a container that comes into contact with a target material.

The hydrogel bead may be provided on a porous fibrous base, and a porous transparent film may be disposed on a surface of the hydrogel bead.

According to one or more embodiments,
a container includes the above-described chemical sensor.

According to one or more embodiments,
an electronic product includes the above-described container.

The electronic product may further include: a controller configured to collect a color sensed by the chemical sensor and determine a state of food; and a display unit configured to display the state of food determined by the controller.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 3B is a side view of the pocket-type chemical sensor of FIG. 3A;

FIG. 7 is a graph showing the water content of each of the single type of hydrogel beads according to Examples 1 and 3;

FIG. 8 is a graph showing the water content of each of the single type or core-shell type of hydrogel beads according to Examples 2, 4, 5, and 6;

DETAILED DESCRIPTION

Figure 1A:
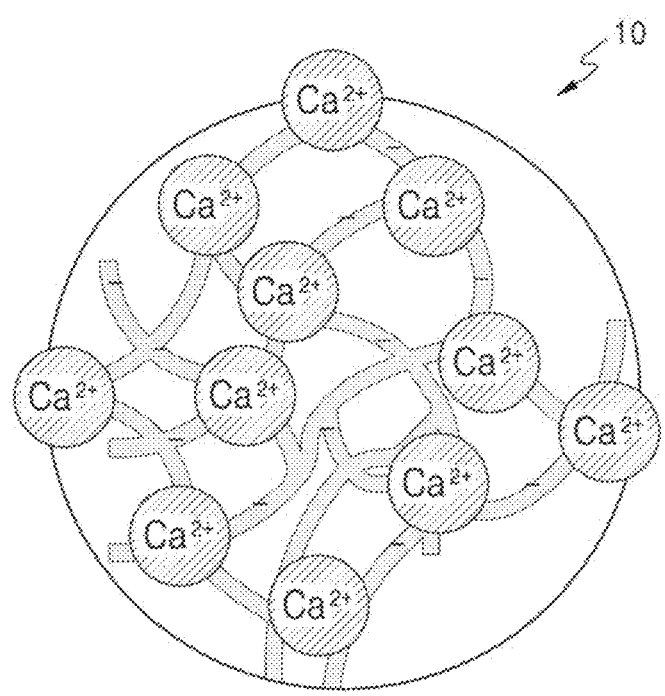
FIG. 1A is a view of a single type of hydrogel bead according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Hereinafter, a hydrogel bead according to an example embodiment, a chemical sensor including the same, and a container and electronic product including the chemical sensor will be described in detail with reference to the accompanying drawings. Embodiments set forth herein are provided for illustrative purposes only and are not intended to limit the present disclosure, and the present disclosure should be defined only by the appended claims.

As used herein, the term "hydrogel bead" means "a bead with water in which a crosslinked structure of a polysaccharide crosslinked with a cation or an anion is introduced," and refers to a bead-type structure which has high permeability and swells by including an aqueous solution therein.

As used herein, the expression "single-bead type" means "a bead type consisting of one type of polysaccharide crosslinked with a cation or an anion."

As used herein, the expression "core-shell bead type" means "a bead type including, as a core, one type of polysaccharide crosslinked with a cation or an anion, the core being coated with another type of polysaccharide that is different from the one type of polysaccharide."

In the food field, a portable electronic nose capable of detecting the freshness and spoilage of food by sensing the amount of a volatile organic compound has been developed. The portable electronic nose is easy to carry, but a device for detection and smartphone equipment for monitoring are required.

In addition, as a sensor for detecting acetic acid generated during the fermentation process of kimchi, a sensor including, on a support of a hydrophilic membrane such as cellulose ester or glass fiber, a moisture absorbent such as glycerin or ethylene glycol and a pH indicator dye is attached to a sealed container and used. However, such a sensor can be used only in the corresponding container, and for use as a sensor, it is required for a user to perform a process of immersing the sensor in water and drying the sensor.

To address these, the inventors of the present disclosure have proposed a hydrogel bead according to an embodiment, which will be described below, a chemical sensor including the same, and an electronic product including the chemical sensor.

A hydrogel bead according to an embodiment may include: at least one type of polysaccharide physically crosslinked with a cation or an anion; and a pH indicator dye.

The hydrogel bead according to an embodiment includes, therein, a polysaccharide consisting of a material that is harmless to the environment and biocompatible, the polysaccharide being physically crosslinked with a cation or an anion, and includes a pH indicator dye, and thus may have an improved ability to detect harmful substances (or a target material) through visible color conversion.

The hydrogel bead may include a single-bead type, a core-shell bead type, or a combination thereof.

Figure 1B:
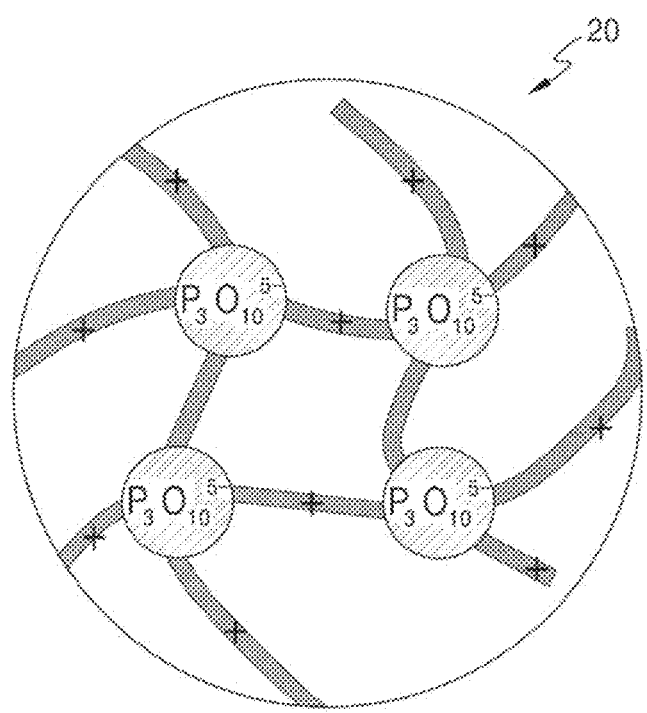
FIG. 1B is a view of a single type of hydrogel bead according to another embodiment.

FIG. 1A is a view of a single type of hydrogel bead 10 according to an embodiment. FIG. 1B is a view of a single type of hydrogel bead 20 according to another embodiment.

Referring to FIG. 1A, the hydrogel bead 10 may include a polysaccharide physically crosslinked with $Ca^{2+}$ ions. Referring to FIG. 1B, the hydrogel bead 20 may include a polysaccharide physically crosslinked with $P_3O_{10}^{5-}$ ions. In the hydrogel bead 10 or 20, a pH indicator dye (not shown) may be distributed in the structure of at least one type of polysaccharide physically crosslinked with a cation (e.g., $Ca^{2+}$ ions) or an anion (e.g., $P_3O_{10}^{5-}$ ions).

When the single type of hydrogel bead according to an embodiment is exposed to a material such as a liquid and/or a gas generated according to the putrefaction or fermentation of food, e.g., kimchi, the material is ionized in an aqueous solution inside the bead. As a result, pH inside the bead and the color of the bead are changed, thus enabling a user to easily observe the putrefaction or fermentation of food, in addition to the stability thereof.

Figure 2:
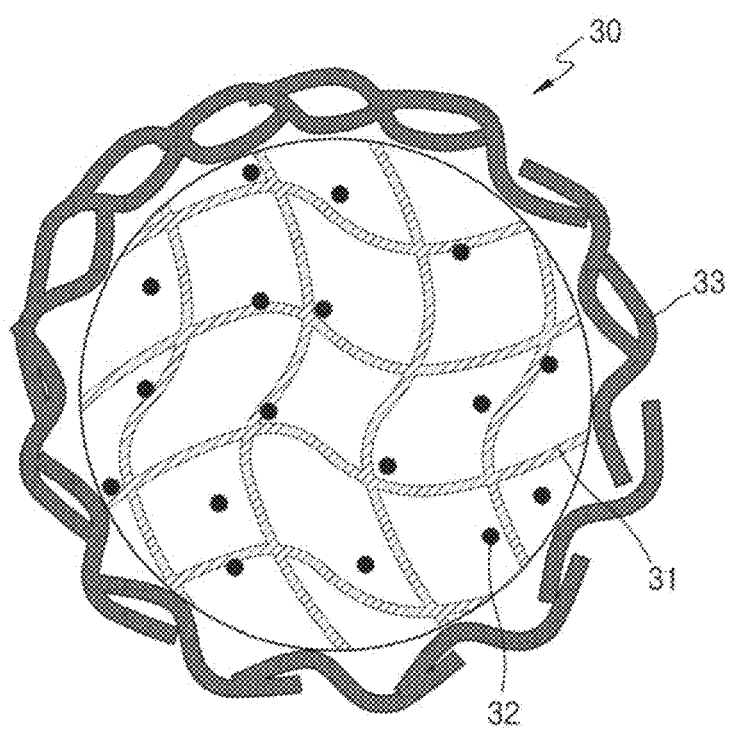
FIG. 2 is a view of a core-shell type of hydrogel bead according to an embodiment.

FIG. 2 is a view of a core-shell type of hydrogel bead 30 according to an embodiment. Referring to FIG. 2, the core-shell type of hydrogel bead 30 may consist of: a core including a first polysaccharide 31 physically crosslinked with the cation and a pH indicator dye 32; and a shell including, on the core, a second polysaccharide 33 that is non-crosslinked. The cation may include $Ca^{2+}$. In another embodiment, a core-shell type of hydrogel bead according to an embodiment may consist of: a core including a second polysaccharide physically crosslinked with the anion and a pH indicator dye; and a shell including, on the core, a first polysaccharide that is non-crosslinked. The anion may include $P_3P_{10}^{5-}$. The polysaccharide may include alginate, chitosan, or a combination thereof.

The shell of the core-shell type of hydrogel bead according to an embodiment may prevent the pH indicator dye 32 included inside the bead from being dispersed outside the core, and may enhance the overall structural stability of the bead. In addition, since the core-shell type of hydrogel bead includes, in the shell, a small amount of the second polysaccharide 33 that is non-crosslinked, a user may easily observe changes in pH inside the bead and the color of the bead.

The pH indicator dye may cause color conversion when a target material is diffused in an aqueous solution inside the hydrogel bead. The pH indicator dye is able to detect color conversion inside the bead, caused by a pH change due to $H^+$ ions generated by diffusion of a target material such as a liquid and/or a gas generated during the fermentation of food, e.g., kimchi.

The target material may include carbon dioxide, acetic acid, ammonia, or a combination thereof. For example, in the case where the target material is acetic acid, when the hydrogel bead is exposed to an acetic acid solution or a gas, the acetic acid solution or the gas is decomposed into $H^+$ ions on the right side as shown in Reaction Scheme 1 below.

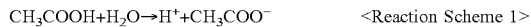

$CH_3COOH+H_2O \rightarrow H^+ + CH_3COO^-$  <Reaction Scheme 1>

The pH indicator dye in the hydrogel bead may cause color conversion due to a pH change within a pH ranging from 3.5 to 6.0.

For example, the pH indicator dye may be selected from bromophenol blue (BPB), bromothymol blue (BTB), bromocresol purple (BCP), bromocresol green (BCG), meta-cresol purple (mCP), and a mixture thereof.

The bead may have a diameter of about 200 µm to 3 mm, for example, about 500 µm to 2 mm.

The single type and/or core-shell type of hydrogel bead has a three-dimensional structure. The single type and/or core-shell type of hydrogel bead has a relatively very large internal and/or external surface area, as compared to hydrogel films, and thus enables a user to easily observe a color change in the bead regardless of the direction. Accordingly, the ability to detect a target material generated from food may further be enhanced.

The hydrogel bead may have a water content of $1 \times 10^3\%$ or more. For example, the water content of the hydrogel bead may be $2 \times 10^3\%$ or more. Of the hydrogel beads, in the core-shell type of hydrogel bead, as the amount of the second polysaccharide 33 that is provided in the shell and non-crosslinked or the first polysaccharide that is non-crosslinked increases, the strength of the bead may be increased, whereas the content of water in the bead may be reduced. Thus, by changing the amount of the shell of the core-shell type of hydrogel bead according to the target material, the sensitivity of the hydrogel bead may be adjusted.

A chemical sensor according to another embodiment may include the above-described hydrogel bead.

The chemical sensor may include a patch-type chemical sensor, a pouch-type chemical sensor, a pocket-type chemical sensor, or a combination thereof.

Figure 3A:
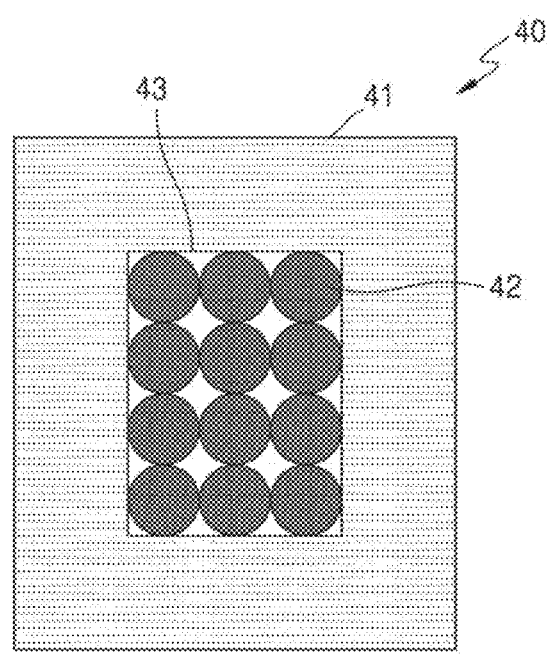
FIG. 3A is a top view of a pocket-type chemical sensor according to an embodiment.

FIG. 3A is a top view of a pocket-type chemical sensor 40 according to an embodiment. FIG. 3B is a side view of a pocket-type chemical sensor 50.

Referring to FIGS. 3A and 3B, the pocket-type chemical sensor 40 or 50 according to an embodiment has a structure in which hydrogel beads 42 or 52 are provided on a porous fibrous base 41 or 51, and a porous transparent film 43 or 53 is disposed on the hydrogel beads 42 or 52. The porous fibrous base 41 or 51 may be, for example, non-woven fabric or the like. The porous transparent film 43 or 53 may be, for example, cellulose or the like. The pocket-type chemical sensor may use the porous fibrous base 41 or 51 and/or the porous transparent film 43 or 53, thereby facilitating dispersion of a target material in the beads.

The hydrogel beads may be provided on an inner surface of a container that comes into contact with the target material, without a support. The chemical sensor is portable.

The chemical sensor may detect the fermentation degree, putrefaction of food, or spoilage degree.

A container according to another embodiment may include the above-described chemical sensor.

An electronic product according to another embodiment may include the above-described container. The electronic product may be used in a refrigerator, for example, a kimchi refrigerator.

The chemical sensor may be arranged, without a support, on the inner surface of a container positioned in an electronic product. In addition, as necessary, the chemical sensor may be directly installed inside an electronic product.

The electronic product may further include a controller configured to collect a color sensed by the chemical sensor and determine a state of food, and a display unit configured to display the state of food determined by the controller. For example, since the amount of target material generated varies depending on the fermentation degree, putrefaction of food, or spoilage degree, the controller may store, as database, the amount of the target material and determine the fermentation degree, putrefaction of food, or spoilage degree, corresponding to an output signal of the chemical sensor. By displaying the state of food determined by the controller on the display unit positioned outside an electronic product, a user may identify the state of food in the electronic product.

Hereinafter, examples of the present disclosure will be described. However, these examples are provided for illustrative purposes only and are not intended to limit the present disclosure.

EXAMPLES

Example 1: Preparation of Single Type of Hydrogel Bead

An aqueous alginate solution in which 1 wt % of sodium alginate was dispersed in deionized water was prepared. 4 mM bromocresol green (BCG) as a pH indicator dye was dispersed in the aqueous alginate solution, thereby preparing a mixed aqueous solution. The mixed aqueous solution was sprayed into a 0.1 M calcium chloride solution via nozzles with a size of 22 G by using an electric spray device equipped with a voltage transformer (230 High Voltage Power Supply, manufactured by Spellman) and a syringe pump (KDS100, manufactured by KD Scientific) and applying a voltage of 15 kV thereto to cause crosslinking for about 10 minutes, followed by washing with deionized water, thereby completing the preparation of a single type of alginate hydrogel bead (diameter: about 800 µm) containing a pH indicator dye.

Example 2: Preparation of Single Type of Hydrogel Bead

A single type of alginate hydrogel bead (diameter: about 800 µm) containing a pH indicator dye was prepared in the same manner as in Example 1, except that 2 wt % of sodium alginate was used instead of 1 wt % of sodium alginate.

Example 3: Preparation of Single Type of Hydrogel Bead

An aqueous chitosan solution in which 1 wt % of chitosan was dispersed in deionized water was prepared. 4 mM BCG as a pH indicator dye was dispersed in the aqueous chitosan solution, thereby preparing a mixed aqueous solution. The mixed aqueous solution was sprayed into a 0.1 M $Na_5P_3O_{10}$ solution via nozzles with a size of 27 G by using an electric spray device equipped with a voltage transformer (230 High Voltage Power Supply, manufactured by Spellman) and a syringe pump (KDS100, manufactured by KD Scientific) and applying a voltage of 10 kV thereto to cause crosslinking for about 10 minutes, followed by washing with deionized water, thereby completing the preparation of a single type of chitosan hydrogel bead (diameter: about 500 μm) containing a pH indicator dye.

Example 4: Preparation of Core-Shell Type of Hydrogel Bead

The single type of alginate hydrogel bead containing a pH indicator dye prepared according to Example 2 was impregnated with 0.1 wt % of an aqueous chitosan solution for 10 minutes to thereby prepare a core-shell type of hydrogel bead (diameter: about 500 μm) including, as a core, the alginate hydrogel bead containing a pH indicator dye and a shell formed by coating non-crosslinked chitosan onto the core.

Example 5: Preparation of Core-Shell Type of Hydrogel Bead

A core-shell type of hydrogel bead (diameter: about 800 μm) including, as a core, an alginate hydrogel bead containing a pH indicator dye and a non-crosslinked chitosan shell was prepared in the same manner as in Example 4, except that the single type of alginate hydrogel bead containing a pH indicator dye prepared according to Example 2 was impregnated with 0.5 wt % of an aqueous chitosan solution, instead of 0.1 wt % of an aqueous chitosan solution, for 10 minutes.

Example 6: Preparation of Core-Shell Type of Hydrogel Bead

A core-shell type of hydrogel bead (diameter: about 800 μm) including, as a core, an alginate hydrogel bead containing a pH indicator dye and a non-crosslinked chitosan shell was prepared in the same manner as in Example 4, except that the single type of alginate hydrogel bead containing a pH indicator dye prepared according to Example 2 was impregnated with 1.0 wt % of an aqueous chitosan solution, instead of 0.1 wt % of an aqueous chitosan solution, for 10 minutes.

Comparative Example 1: Preparation of Hydrogel Film

An aqueous alginate solution in which 1 wt % of sodium alginate was dispersed in deionized water was prepared. 4 mM BCG as a pH indicator dye was dispersed in the aqueous alginate solution, thereby preparing a mixed aqueous solution.

A drop of the mixed aqueous solution was sprayed onto a slide glass fixed to a table via a tape, using a needle with a size of 18 G, and then uniformly spread thereon using a glass pipette.

The slice glass on which the mixed aqueous solution was spread was immersed in a 1.0 M calcium chloride solution for about 3 seconds and taken out thereof, followed by washing with deionized water, thereby completing the preparation of an alginate hydrogel film containing a pH indicator dye.

Analysis Example 1: Confirmation of Structures and Diameters of Hydrogel Beads The singe type of hydrogel beads prepared according to Examples 1 and 3 were observed using an optical microscope. The results thereof are illustrated in FIGS. 4 and 5, respectively.

Figure 4:
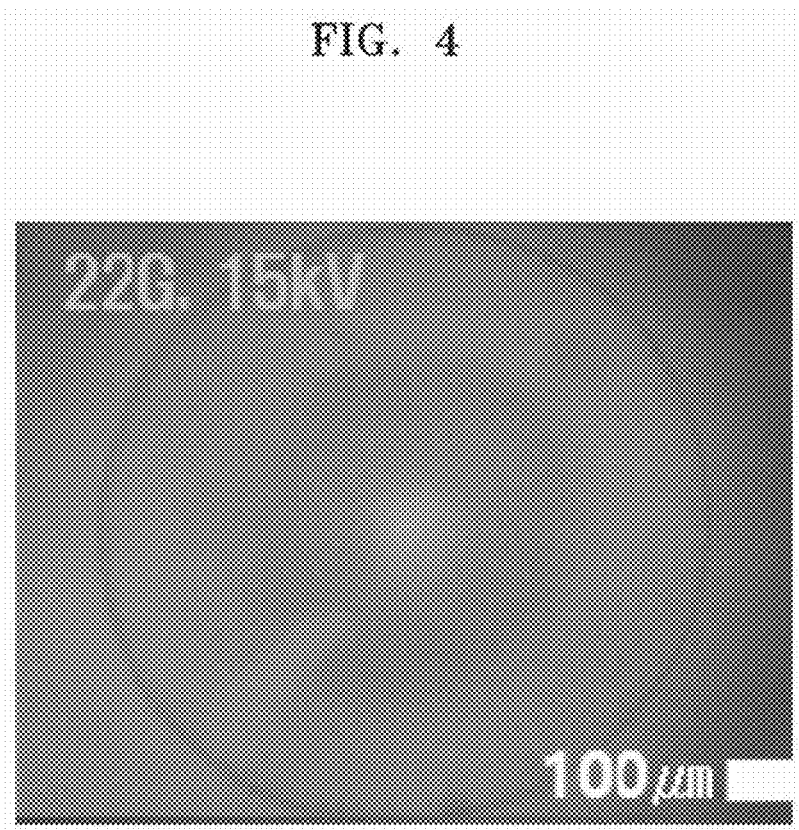
FIG. 4 is an optical microscope image showing a single type of hydrogel bead according to Example 1.
Figure 5:
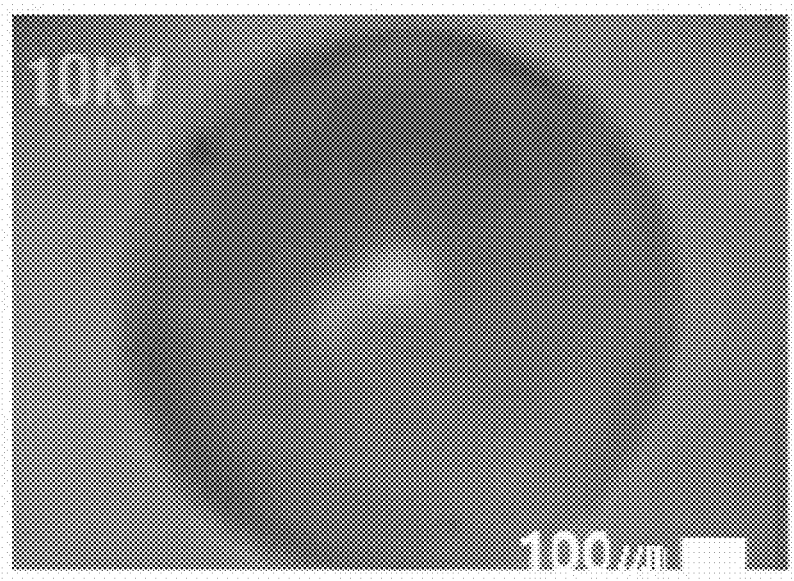
FIG. 5 is an optical microscope image showing a single type of hydrogel bead according to Example 3.

Referring to FIGS. 4 and 5, it can be confirmed that both the hydrogel bead of Example 1 and the hydrogel bead of Example 3 were a single-bead type. It can also be confirmed that the single type of hydrogel beads of Examples 1 and 3 had a diameter of about 800 μm and about 500 μm, respectively.

In addition, the single type or core-shell type of hydrogel beads prepared according to Examples 2, 4, 5, and 6 were observed using an optical microscope. The results thereof are illustrated in FIGS. 6A to 6D, respectively.

Figures 6A, 6B, 6C, 6D:
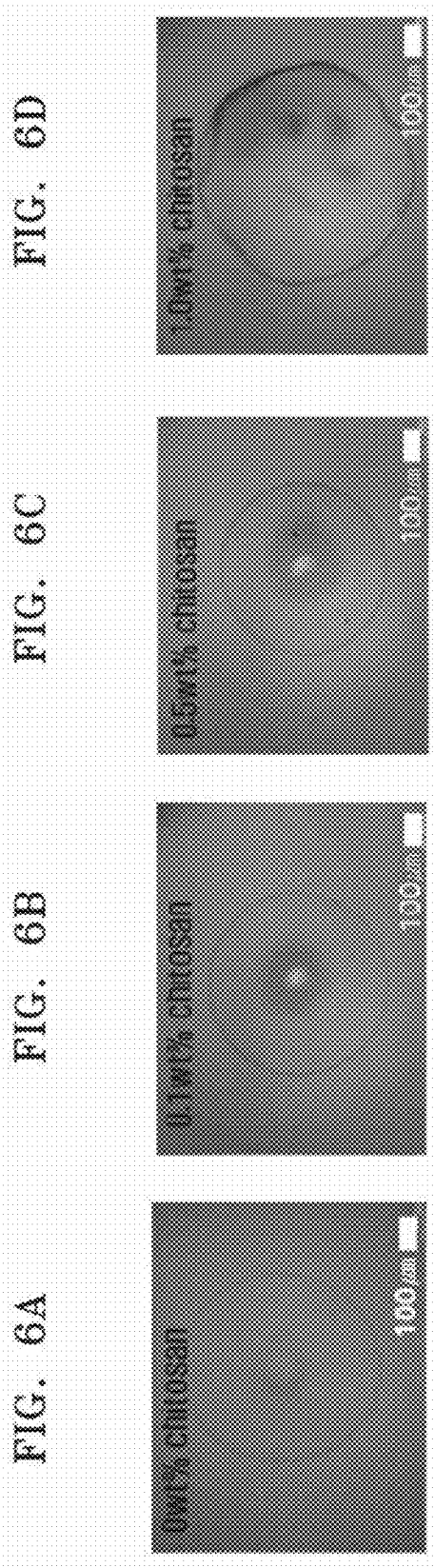
FIGS. 6A to 6D are optical microscope images of single type or core-shell type of hydrogel beads according to Examples 2, 4, 5, and 6.

Referring to FIG. 6A, it can be confirmed that the hydrogel bead of Example 2 was a single-bead type. Referring to FIGS. 6B and 6C, it can be confirmed that both the hydrogel beads of Examples 4 and 5 were a core-shell bead type. At this time, it can be confirmed that the core-shell type of hydrogel beads of Examples 4 and 5 had a diameter of about 500 μm and about 800 μm, respectively.

Referring to FIG. 6D, it can be confirmed that the hydrogel bead of Example 6 was a core-shell bead type, but was out of shape due to a low content of water in the core.

Analysis Example 2: Water Content Analysis

The water content of each of the single type of hydrogel beads of Examples 1 and 3, and the single type or core-shell type of hydrogel beads of Examples 2, 4, 5, and 6 was analyzed. In this regard, in an equilibrium state (in deionized water), the swelling time of the single type or core-shell type of hydrogel beads was fixed to 8 hours, and the water content was calculated using Equation 1 below. The results thereof are illustrated in FIG. 7

$$\text{Water content (\%)} = [(\text{Mass of swollen bead} - \text{mass of dried bead})/(\text{mass of dried bead}) \times 100] \quad [\text{Equation 1}]$$

Referring to FIG. 7, the single type of hydrogel beads of Examples 1 and 3 exhibited a water content of about $6 \times 10^3\%$ and about $2.8 \times 10^3\%$, respectively.

Referring to FIG. 8, the single type of hydrogel bead of Example 2 exhibited a water content of about $3.3 \times 10^3\%$, and the core-shell type of hydrogel beads of Examples 4 and 5 exhibited a water content of about $6 \times 10^3\%$ and about $4 \times 10^3\%$, respectively.

The core-shell type of hydrogel bead of Example 6 exhibited a water content of about $2.8 \times 10^3\%$. The reason why the core-shell type of hydrogel bead of Example 6 exhibited a reduced water content is considered to be due to the formation of a bond caused by the electrostatic attraction (particularly, electrostatic attraction between $NH^{3+}$ ions and $COO^-$ ions) between the alginate hydrogel bead as a core and the non-crosslinked chitosan shell.

Evaluation Example 1: Chemical Sensor Detection Evaluation

When adding dropwise each of acetic acid solutions of pH 2, pH 4, and pH 6 to the single type of hydrogel bead of Example 1, the color conversion of each bead was observed using a camera (manufactured by Nikon, VH-310G2). The results thereof are illustrated in FIGS. 9A, 9B, and 9C, respectively.

Figures 9A, 9B, 9C:
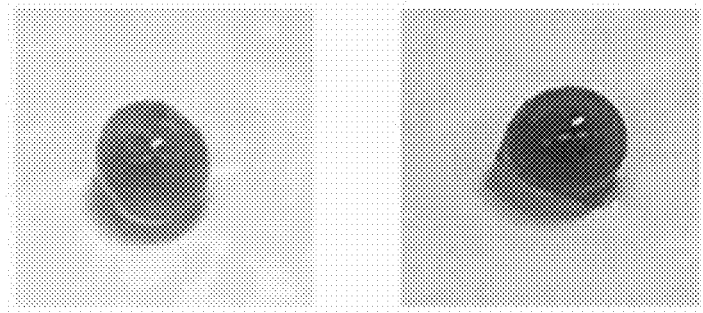
FIGS. 9A to 9C are images respectively showing color changes in the single type of hydrogel bead according to Example 1 when adding dropwise acetic acid solutions of pH 2, pH 4, and pH 6 thereto.

Referring to FIGS. 9A to 9C, it can be confirmed that, when each of acetic acid solutions of pH 2, pH 4, and pH 6 was added dropwise to the single type of hydrogel bead of Example 1 using a pipette, the respective beads showed remarkable changes in color into yellow, green, and dark blue in accordance with the pH change.

When adding dropwise each of acetic acid solutions of pH 4 and pH 6 to the hydrogel film prepared according to Comparative Example 1, the color conversion of each film was observed using a camera (manufactured by Nikon, VH-310G2). The results thereof are illustrated in FIGS. 10A and 10B, respectively.

Figure 10A:
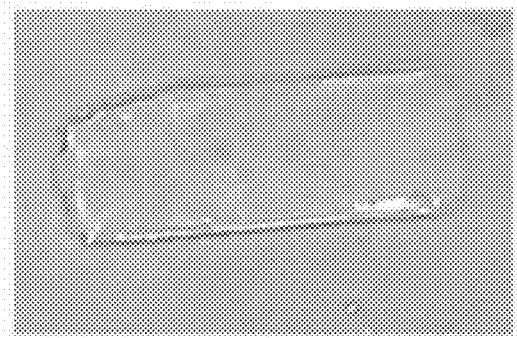
FIGS. 10A and 10B are images respectively showing color changes in a hydrogel film according to Comparative Example 1 when adding dropwise acetic acid solutions of pH 4 and pH 6 thereto.
Figure 10B:
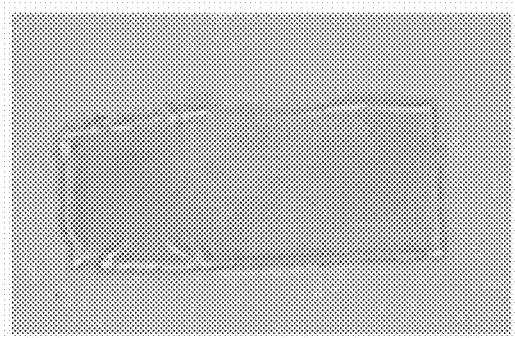

Referring to FIGS. 10A and 10B, it can be confirmed that, when adding dropwise each of acetic acid solutions of pH 4 and pH 6 to the hydrogel film of Comparative Example 1 using a pipette, the respective films showed changes in color from white to light blue in accordance with the pH change.

From these results, it can be seen that the single type of hydrogel bead of Example 1 is capable of clearly detecting an acetic acid solution within a wide range of pH, as compared to the hydrogel film of Comparative Example 1.

As is apparent from the foregoing description, a hydrogel bead according to an embodiment includes a pH indicator dye, and thus causes a pH change in the bead and color conversion, due to harmful substances (or a target material) generated from food, thereby easily detecting the fermentation degree, putrefaction of food, spoilage degree. In addition, a chemical sensor including the hydrogel bead is portable, and can be attached to the inner surface of a container and reused, thus being capable of contributing to the widespread use thereof.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. A chemical sensor comprising a hydrogel bead comprising:
    at least one type of polysaccharide physically crosslinked with a cation or an anion; and
    a pH indicator dye,
    wherein the hydrogel bead is a core-shell bead,
    wherein the hydrogel bead is arranged, without a support, on an inner surface of a container that comes into contact with a target material, or the hydrogel bead is provided on a porous fibrous base, and a porous transparent film is disposed on a surface of the hydrogel bead, and
    wherein the pH indicator dye is a dye that causes color conversion when a target material is diffused in an aqueous solution inside the hydrogel bead.

2. The chemical sensor of claim 1, wherein the pH indicator dye is distributed in the at least one type of polysaccharide physically crosslinked with a cation or an anion.

3. The chemical sensor of claim 1, wherein the hydrogel bead is a core-shell bead consisting of:
    a core comprising a first polysaccharide physically crosslinked with the cation and a pH indicator dye; and
    a shell comprising, on the core, a second polysaccharide, the second polysaccharide being non-crosslinked.

4. The chemical sensor of claim 1, wherein the hydrogel bead is a core-shell bead consisting of:
    a core comprising a second polysaccharide physically crosslinked with the anion and a pH indicator dye; and
    a shell comprising, on the core, a first polysaccharide, the first polysaccharide being non-crosslinked.

5. The chemical sensor of claim 1, wherein the cation comprises $Ca^{2+}$.

6. The chemical sensor of claim 1, wherein the anion comprises $P_3O_{10}^{5-}$.

7. The chemical sensor of claim 1, wherein the at least one type of polysaccharide comprises alginate, chitosan, or a combination thereof.

8. The chemical sensor of claim 1, wherein the target material comprises carbon dioxide, acetic acid, ammonia, or a combination thereof.

9. The chemical sensor of claim 1, wherein the pH indicator dye is a dye that causes color conversion within a pH ranging from about 3.5 to about 6.0.

10. The chemical sensor of claim 1, wherein the pH indicator dye is selected from bromophenol blue (BPB), bromothymol blue (BTB), bromocresol purple (BCP), bromocresol green (BCG), metacresol purple (mCP), and a mixture thereof.

11. The chemical sensor of claim 1, wherein the chemical sensor comprises a patch chemical sensor, a pouch chemical sensor, a pocket chemical sensor, or a combination thereof.

12. A container comprising the chemical sensor of claim 1.

13. An electronic product comprising the container of claim 12.

14. The electronic product of claim 13, further comprising:
    a controller configured to collect a color sensed by the chemical sensor and determine a state of food; and
    a display unit configured to display the state of food determined by the controller.

* * * * *